(12) United States Patent
Wu et al.

(10) Patent No.: US 6,872,692 B2
(45) Date of Patent: Mar. 29, 2005

(54) SYNTHETIC HYDROCARBON FLUID

(75) Inventors: Margaret May-Som Wu, Skillman, NJ (US); Steven Edward Donnachie, Clayton, NJ (US); James Thomas Carey, Medford, NJ (US); Walter David Vann, Marlton, NJ (US); Norman Yang, Westfield, NJ (US); Dilip Surana, Somerset, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 133 days.

(21) Appl. No.: 10/238,173

(22) Filed: Sep. 10, 2002

(65) Prior Publication Data

US 2003/0114320 A1 Jun. 19, 2003

Related U.S. Application Data

(60) Provisional application No. 60/324,082, filed on Sep. 21, 2001.

(51) Int. Cl.$^7$ ............................................. C10M 107/12
(52) U.S. Cl. ........................ 508/110; 508/591; 585/11; 585/19; 208/18
(58) Field of Search ............................ 508/110; 585/11, 585/19

(56) References Cited

U.S. PATENT DOCUMENTS

| | | | |
|---|---|---|---|
| 2,474,881 A | 7/1949 | Young et al. | ............... 260/668 |
| 2,500,203 A | 3/1950 | Reiff et al. | ................. 260/666 |
| 3,448,050 A | 6/1969 | Young et al. | ................. 252/59 |
| 4,162,985 A * | 7/1979 | Holubec | ...................... 585/11 |
| 4,677,176 A | 6/1987 | Evans et al. | ................ 526/290 |
| 4,933,409 A | 6/1990 | Evans et al. | ................ 526/290 |
| 4,967,029 A | 10/1990 | Wu | ............................ 585/12 |
| 5,030,791 A | 7/1991 | Sanderson et al. | .......... 585/533 |
| 6,214,779 B1 * | 4/2001 | Kaneshige et al. | ......... 508/591 |

FOREIGN PATENT DOCUMENTS

| | | | |
|---|---|---|---|
| DE | 19915904 | 12/2000 | |
| EP | 0902081 | 3/1999 | ........ C10M/107/12 |
| EP | 0974570 | 1/2000 | ............. C07C/2/68 |
| EP | 1059313 | 12/2000 | ......... C08F/210/02 |
| GB | 2036761 | 7/1980 | ........... C08F/10/00 |
| SU | 1068467 A | 1/1984 | |
| WO | 9626913 | 9/1996 | ............. C07C/2/20 |
| WO | 9830519 | 7/1998 | ............. C07C/2/04 |
| WO | 9830520 | 7/1998 | ............. C07C/2/04 |
| WO | 9830521 | 7/1998 | ............. D07C/2/04 |
| WO | 9830587 | 7/1998 | ......... C07K/14/435 |

OTHER PUBLICATIONS

Smalheer et al "Lubricant Additives", Section I—Chemistry of Additives, pp. 1–11, 1967.*

* cited by examiner

*Primary Examiner*—Ellen M. McAvoy
(74) *Attorney, Agent, or Firm*—Charles J. Brumlik

(57) ABSTRACT

A synthetic lubricant base stock is provided having a kinematic viscosity at 100° C. of from 5 to about 300 cS and a VI greater than 100. The base stock comprises random co-oligomers of an alpha olefin or mixtures thereof and an olefinic substituted aromatic compound which co-oligomers are prepared in the presence of a Friedel-Crafts catalyst.

20 Claims, No Drawings

SYNTHETIC HYDROCARBON FLUID

This application claims the benefit of U.S. Provisional Application 60/324,082 filed Sep. 21, 2001.

FIELD OF INVENTION

This invention is concerned with improvements in synthetic lubricant base stocks comprising alpha-olefin and vinyl aromatic moieties. More particularly this invention relates to lubricants that exhibit improved properties such as solvency, dispersancy and oxidative stability.

BACKGROUND OF INVENTION

Poly-alpha-olefins (PAOs) produced by oligomerizing alpha-olefins have many unique properties rendering them useful as lubricant base stocks. For example, PAOs typically have high viscosity indicies (VIs), low pour points and can be prepared with a range of viscosities.

Notwithstanding their generally superior properties, PAO lubricants are formulated with additives to enhance those properties for specific applications. The additives which are more commonly used in lubricants include oxidation inhibitors, rust inhibitors, metal passivators, antiwear agents, extreme pressure additives, pour point depressant, detergent-dispersants, viscosity index improvers, antifoamants and the like. However, as is known, PAOs by themselves generally have a low solvency for many additives, especially polar additives. Also, PAOs by themselves tend to have poor dispersancy for sludges generated during use. Consequently, polar base stocks such as polyester fluids are often combined with PAOs to provide solvency and dispersancy to the formulated lubricant. Addition of polar base stocks, however, can complicate preparing a fully formulated lubricant and may introduce other undesirable affects such as the hydrolytic instability associated with polyester base stocks.

Adding to the complexity of formulating lubricating oils is the trend to ever higher oil performance standards dictated by the increasing complexity of newer equipment and engines.

One object of the invention therefor is to improve the solvency of PAO base stocks. Another object of the invention is to improve the dispersancy of PAO base stocks.

SUMMARY OF INVENTION

In one embodiment the present invention relates to a synthetic lubricant base stock having a kinematic viscosity at 100° C. of from 5 to about 300 cS and a viscosity index (VI) greater than 100 and comprising random co-oligomers of an alpha-olefin or mixture thereof and an olefinic substituted aromatic compound having the formula

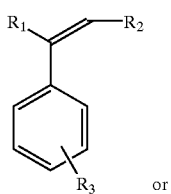

or

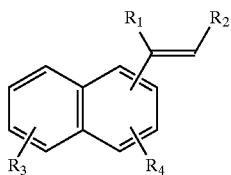

where $R_1$, $R_2$, $R_3$ and $R_4$ are independently H or a $C_1$ to $C_4$ alkyl group.

In another embodiment the invention relates to a process for the preparation of a synthetic lubricant base stock by oligoinerizing an alpha-olefin or mixtures thereof and an olefinic substituted aromatic compound of formula I or II in the presence of a Friedel-Crafts catalyst under conditions sufficient to form substantially random co-oligomers.

In yet another embodiment the co-oligomers are treated with an aromatic compound to provide a base stock comprising aromatic end-capped co-oligomers.

Other aspects and embodiments of the invention will become apparent upon reading the detailed description which follows.

DETAILED DESCRIPTION OF THE INVENTION

In the present invention alpha-olefins are co-oligomerized with olefinic substituted aromatic monomers in the presence of a Friedel-Crafts catalyst to produce co-oligomers useful as a lubricant base stock without further treatment or which can be further treated with an aromatic compound to yield a product also useful as a lubricant basestock.

The alpha-olefins suitable for use in the present invention include $C_6$ to $C_{12}$ alpha-olefins and preferably from $C_8$ to $C_{10}$ alpha-olefins or mixture of $C_6$ to $C_{20}$ alpha olefin with at least 50% of the mixture having olefins of less than 12 carbon atoms.

The olefinic substituted aromatic compounds useful herein are represented by the general formula

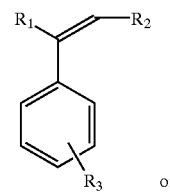

or

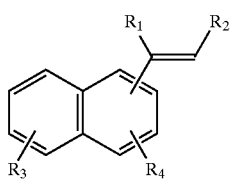

wherein $R_1$, $R_2$, $R_3$ and $R_4$ are independently H or a $C_1$ to $C_4$ alkyl group.

Examples of especially suitable olefinic substituted aromatic compounds include styrene, para-methylstyrene, para-ethylstyrene, meta-methylstyrene, meta-ethylstyrene, ortho-methylstyrene, ortho-ethylstyrene, alpha-methylstyrene, beta-metylstyrene, vinyl naphthalene, and vinyl-alkylnaphthalenes such as vinyl methylnaphthalene.

The catalyst useful in the co-oligomerization process of the invention includes all of the metal and metalloid halides conventionally used as Friedel-Crafts catalysts. Suitable examples include $AlCl_3$, $BF_3$, $AlBr_3$, $TiCl_3$, $TiCl_4$, $SbCl_3$, $SbCl_5$, $SnCl_4$, $VOCl_3$, or the promoted catalysts and the like. $AlCl_3$ is the preferred Friedel-Crafts catalyst.

The co-oligomers of the present invention are prepared by contacting the olefinic substituted aromatic compound and the alpha-olefin or mixture of olefins with the Friedel-Crafts catalyst under conditions sufficient to form oligomers consisting substantially of random co-oligomers. This can be achieved, for example, by continuously feeding the reactants into and removing the co-oligomers from a reaction zone under steady state conditions with an average residence time of reactants ranging from about 0.1 to about 10 hours and preferably from 0.5 to 5 hours at temperatures sufficient for co-oligomerization to occur.

Optionally the reactants can be introduced substantially simultaneously into a reaction zone over an extended period of time and at a temperature sufficient for co-oligomerization to occur. In general the rate at which the reactants are introduced into the reaction zone will be chosen to maintain the reaction temperature at the requisite level for co-oligomerization to occur. Typical feed rates are 1 part per hour for the catalyst, 50 to 2000 parts per hour and preferably 20 to 1000 parts per hour for the olefin or mixture of olefins and 1 to 1000 parts per hour and preferably 1 to 500 parts per hour for the olefinic aromatic compound.

Typically a mixture of the olefinic aromatic compound and olefin or mixture of olefins is used.

The amount of olefinic substituted aromatic compound used is generally in the range of about 1 wt % to about 80 wt % and preferably from about 2 wt % to about 55 wt % with the amount of olefin or mixture of olefins being from about 99 wt % to about 20 wt % and preferably form about 98 wt % to about 45 wt %.

In general between about 0.1 to about 10 wt % and preferably between about 0.2 to about 3 wt %, based on total feed, of the Friedel-Crafts catalyst is used in the co-oligomerization process.

Solvents or diluents may be used in the co-oligomerization process. These are chemically inert, non-polar liquids at co-oligomerization temperatures such as saturated aliphatic and alicyclic hydrocarbons of which hexane, hexadecane, cyclohexane, and methyl cyclohexane are representative examples. The volume of solvent or diluent can be between about 5 vol % and about 300 vol % of the volume of co-oligomerization feed.

The co-oligomerization reaction temperature can vary between about $-10°$ C. to about $150°$ C., preferably between about $0°$ C. to about $75°$ C. Pressures can vary between about 1 to about 500 psig, and preferably 1 to 100 psig.

After completion of the co-oligomerization reaction the co-oligomer product may be further treated with an aromatic compound and alkyl derivatives having 6 to 20 carbon such as benzene, toluene, naphthalene and the like, and mixtures thereof. In this instance, the amount of aromatic compound or alkyl derivation thereof used may vary widely. Typically the amount of aromatic compound or alkyl derivative used will range from about 5 to about 300 wt % based on the weight of the co-oligomer product and preferably from about 10 to about 50 wt %. The co-oligomerization product is treated in the presence of a Friedel-Crafts catalyst with the aromatic or alkyl aromatic compound at temperatures in the range of about $0°$ C. to about $100°$ C. and preferably $10°$ C. to $60°$ C. for a time sufficient for the co-oligomerization product and aromatic or alkyl aromatic compound to react whereby an aromatic end-capped oligomer lubricant base stock is obtained. Typical treatment times may between about 1 to about 5 hours. In instances where the co-oligomerization product is treated with the aromatic or alkyl aromatic compound in the same reactor in which the co-oligomerization reaction was conducted, sufficient catalyst will be present in the reactor. In instances where the co-oligomerization is conducted in a continuous reaction the co-oligomer product removed may be charged into another reactor for treatment with the aromatic or alkyl aromatic compounds. In this instance, a Friedel-Crafts catalyst will be added to the reactor charged with the co-oligomer and aromatic or alkyl aromatic compound.

The co-oligomer or the co-oligomer treated with the aromatic or alkyl aromatic compound may be recovered by any conventional means. For example the catalyst activity may be quenched by addition of water or a dilute aqueous base. Preferably aqueous base such as 5 wt % NaOH solution is used. The organic layer may be separated and distilled to remove components other than the base stock.

The co-oligomer isolated from the co-oligomerization process can be further treated by hydrogenation to reduce at least some of the olefinic double bonds, which can be measured by bromine number or iodine index, or the like. This hydrogenation step can be controlled to hydrogenate only the unsaturated olefinic double bond, without changing any of the aromatic groups. Examples of suitable hydrogenating catalysts can be found in U.S. Pat. Nos. 4,851,476, 4,980,331, American Chemical Society Polymer Preprints, 2000, 41 (2) 1525 and Review of Macromolecular Chemical Physics 1995, C35(2), 239. Preferably olefinic double bonds of the co-oligomer product will be hydrogenated to provide a bromine number less than 2.

The co-oligomers prepared according to the present invention have a kinematic viscosity at $100°$ C. of from 5 to about 300 cS and a VI greater than 100 and up to about 175. The co-oligomer also have pour points less than about $-10°$ C.

The co-oligomers of the present invention are substantially random co-oligomers. Indeed the abundance of pure block oligomers present in the co-oligomer prepared according to the invention is less than 3% as determined by field ionization mass spectroscopy.

The synthetic base stock may be used alone in formulating lubricant composition and greases or may be in 2 to 98 wt % with other synthetic base stocks, such as PAO, alkylbenzens, polyalkylene glycol, or with other conventional or non-conventional base stocks, including Group I, II, III or Fischer-Tropsch wax-derived lubricant base stocks. In formulating lubricating composition and greases the base stock in major amount is combined with an effective amount of additives selected from typical lubricant composition additives such as antioxidants, antiwear agents, rust inhibitors, extreme pressure agents, antifoamants, dispersants and VI improvers. Greases are formulated by combining the base stock with a thickener such as a lithium soap or poly urea compound and one or more grease additives selected from antioxidants, antiwear agents, extreme pressure agent and dispersants.

EXAMPLES

In the Examples and Comparative Examples which follow the aniline point reported was determined by ASTM Test Method D611. This method measures the lowest temperature an oil can mix with an equal volume of aniline. The lower the aniline point the greater the solvency of the oil for typical lubricant additives.

The viscosities and VIs were measured according to the ASTM D446 method.

The oxidation stability was determined by the Rotary Bomb Oxidation Test (RBOT), i.e., ASTM 2272.

Example 1

Preparation of Alpha-Methylstyrene (AMS) and 1-decene Copolymer

A solution was prepared by mixing 350 grams 1-decene, 150 grams alpha-methyl styrene and 100 gram hexadecane.

200 grams of this mixture was charged into a 3-liter flask and cooled with ice water. 1 gram AlCl$_3$ was added to this mixture. The remaining 400 grams of the mixture was added slowly over two-hour period together with another 4 grams of AlCl$_3$. At the end of the addition, the temperature was raised to 30° C. for 3 hours. Then, 250 ml of dry toluene was added to the reaction mixture and the reaction temperature was raised to 45° C. for 3 hours. The reaction was then quenched with 5% aqueous sodium hydroxide solution. The organic layer was washed with water, separated and distilled at 140° C./<1 millitorr to remove toluene, hexadecane and any other light components. The product properties are summarized in Table 1. Field ionization mass spectroscopy (FIMS) analysis of the oligomers showed that the fluid contains AMS and 1-decene and is not a blocky copolymer, but quite random. The amount of pure 1-decene or pure AMS trimer, tetramer and pentamer in the mixture are very low, as shown in Table 2.

TABLE 2

Relative abundance of oligomer composition by FIMS

|  | Number of decene units | Number of AMS units | Atomic Mass Units | Abundance in FIMS | % abundance in FIMS |
| --- | --- | --- | --- | --- | --- |
| Dimer | 0 | 2 | 236 | — | 0.0 |
|  | 1 | 1 | 258 | — | 0.0 |
|  | 2 | 0 | 280 | — | 0.0 |
| Trimer | 0 | 3 | 354 | 10 | 2.5 |
|  | 1 | 2 | 376 | 100 | 25.4 |
|  | 2 | 1 | 398 | 15 | 3.8 |
|  | 3 | 0 | 420 | 0 | 0.0 |
| Tetramer | 0 | 4 | 472 | 0 | 0.0 |
|  | 1 | 3 | 494 | 60 | 15.2 |
|  | 2 | 2 | 516 | 100 | 25.4 |
|  | 3 | 1 | 538 | 30 | 7.6 |
|  | 4 | 0 | 560 | 7 | 1.8 |
| Pentamer | 0 | 5 | 590 | 0 | 0.0 |
|  | 1 | 4 | 612 | 0 | 0.0 |
|  | 2 | 3 | 634 | 37 | 9.4 |
|  | 3 | 2 | 656 | 20 | 5.1 |
|  | 4 | 1 | 678 | 13 | 3.3 |
|  | 5 | 0 | 700 | 2 | 0.5 |
|  |  |  |  |  | 100.0 |

These FIMS data showed that the abundances of pure block oligomers are low, generally less than 3%, whereas the copolymers containing almost equal amount of both monomers are always the most predominant components. $C_{13}$-NMR also showed that this fluid is a random copolymer of AMS and 1-decene.

Example 2

Same as Example 1, except the mixture was prepared by mixing 250 grams AMS, 250 grams 1-decene and 100 grams hexadecane.

Example 3

Same as Example 1, except the mixture was prepared by mixing 75 grams AMS, 425 grams 1-decene and 100 gram hexadecane.

Comparative Example 1

Preparation of Pure 1-decene PAO Fluid

The procedure was similar to Example 1 except that no AMS was added to the mixture. After all the 1-decene and AlCl$_3$ were charged, the reaction was continued at 40° C. for 3 hours and then worked up similar to Example 1. The polymer was then isolated by distillation and hydrofinished at 200° C. with 1 wt % nickel on Kieselguhr catalyst for 8 hours at 800 psi H$_2$ pressure. The product properties were summarized in Table 1.

Comparative Example 2

Preparation of poly-1-decene PAO End-Capped with Toluene

The procedure was similar to Example 1 except that no AMS was added to the mixture. The product properties were summarized in Table 1.

The data in Table 1 demonstrates that the Example 1 to 3 products with different level of AMS contents have much lower aniline points (103° C. to 140° C.) by ASTM Test Method D611 than those of the Comparative Examples 1 and 2 (159.6 and 149.5° C.). The lower aniline point is a clear indication that the Examples 1 to 3 products have much higher polarity and therefore, higher solvency and dispersancy than the comparative products. Furthermore, the RBOT (Rotary Bomb Oxidation Test, D2272 method) oxidation time for Examples 1 to 3 is 20 to 44 minutes, which are longer than the RBOT of Comparative Example 1 or 2, indicating that the copolymers of 1-decene and AMS have better oxidative stability.

Comparative Example 3

Preparation of Highly Blocky Co-Polymer by Pure Batch Mode of Operation.

120 gram 1-decene, 830 gram alpha-methylstyrene, 40 gram hexadecane and 20 gram dodecane (as internal standard) were mixed in an one-liter round bottom flask and maintain at 5–10° C. Powder aluminum chloride of 0.5 gram was added to the reactor. After 6 hours, the reaction was stopped and the product was isolated in the same manner as in Example 7. The product had the following properties: V @100° C.=72.69 cS, V @40° C.=3169 cS, VI=56, pour point=+2° C.

Example 4

Preparation of Vinylnaphthalene and 1-decene Copolymer

This product was prepared in similar procedure as Example 1, except that the mixture was prepared from 30 gram 2-vinylnaphthalene, 70 gram 1-decene and 1 gram AlCl$_3$ was used as catalyst. The product properties were summarized in Table 3.

TABLE 1

Lube Properties of Co-Polymers

|  | Example 1 | Example 2 | Example 3 | Comparative Example 1 | Comparative Example 2 |
| --- | --- | --- | --- | --- | --- |
| Aromatic (A) | alpha-methylstyrene | alpha-methylstyrene | alpha-methylstyrene | none | none |
| Wt % aromatics | 30 | 50 | 15 | 0 | 0 |
| O/A mole ratio | 2/1 | 0.8/1 | 4.8/1 | 0 | 1/0 |
| End cap aromatic | toluene | toluene | toluene | none | toluene |
| Lube yield, wt % | >95 | >90 | >90 | — | >90 |
| Lube Properties |  |  |  |  |  |
| V 100° C., cS | 29.2 | 38.02 | 37.05 | 40 | 40.25 |
| V 40° C., cS | 362.3 | 868.8 | 402.5 | 440 | 437.1 |
| VI | 115 | 72 | 137 | 145 | 141 |

TABLE 1-continued

Lube Properties of Co-Polymers

|  | Example 1 | Example 2 | Example 3 | Comparative Example 1 | Comparative Example 2 |
|---|---|---|---|---|---|
| Pour point, ° C. | −30 | −15 | −35 | −34 | −37 |
| Bromine number | 1.5 | 1.1 | 3.4 | 1 | 1.9 |
| Aniline point, ° C. | 117.8 | 103.2 | 140.3 | 159.6 | 149.5 |
| RBOT, minutes | 34 | 44 | 20 | 15 | 18 |

Example 5

This product was prepared in similar procedure as Example 1, except that the mixture was prepared from 20 grams 2-vinylnaphtlhalene, 80 grams 1-decene, and 1 gram AlCl$_3$ was used as catalyst. The product properties are summarized in Table 3.

Example 6

This product was prepared in similar procedure as Example 1, except that the mixture was prepared from 10 grams 2-vinylnaphthalene, 90 grams 1-decene, and 1 gram AlCl$_3$ was used as catalyst. The product properties are summarized in Table 3.

Example 7

This product was prepared in similar procedure as Example 1, except that the mixture was prepared form 5 grams 2-vinylnaphthalene, 95 grams 1-decene, and 1 gram AlCl$_3$ was used as catalyst. The product properties are summarized in Table 3.

TABLE 3

Product properties of vinylnaphthalene and 1-decene copolymers

|  | Comparative Example 1 | Comparative Example 2 | Example 4 | Example 5 | Example 6 | Example 7 |
|---|---|---|---|---|---|---|
| Olefins (O) | 1-C10 | 1-C10 | 1-C10 | 1-C10 | 1-C10 | 1-C10 |
| Aromatics (A) | none | none | 2-vinyl-naphthalene | 2-vinyl-naphthalene | 2-vinyl-naphthalene | 2-vinyl-naphthalene |
| Wt % aromatics | 0 | 0 | 30 | 20 | 10 | 5 |
| O/A mole ratio | 0 | 1/0 | 4.4/1 | 4.4/1 |  |  |
| End cap aromatics | none | toluene | toluene | toluene | toluene | toluene |
| Reaction temperature, ° C. |  | 10–40 | 30–60 | 5–30 | 5–30 | 23–30 |
| Lube yield, wt % |  | >95 | >90 | >90 | 90 | 90 |
| Lube Properties |  |  |  |  |  |  |
| V 100° C., cS | 40 | 40.25 | 83.04 | 89.21 | 72.32 | 55.82 |
| V 40° C., cS | 440 | 437.1 | 2331 | 1904 | 1063 | 706 |
| VI | 145 | 141 | 94 | 114 | 137 | 140 |
| Pour point, ° C. | −34 | −37 | −12 | −17 | −27 | −32 |
| Bromine number | 1 | 1.85 |  | 2.5 | 2.3 | 2 |
| Aniline point, ° C. | 159.6 | 149.5 | 91 | 126.2 | 143.9 | 148.6 |
| RBOT, minutes | 15 | 18 | na | na | 52 | 46 |

Again, the data in Table 3 demonstrates that copolymerization of alpha-olefin with vinylnaphthalene yields lube products with much lower aniline point than the Comparative Examples 1 and 2. Furthermore, the copolymers have much better oxidative stability (longer RBOT time) than comparative examples.

Example 8

This product was prepared in similar procedure as Example 1, except that the mixture was prepared from 12.5 grams styrene and 87.5 grams 1-decene, and 1 gram AlCl$_3$ was used as catalyst. The product properties are summarized in Table 4.

Example 9

Similar to Example 8 except the product was prepared from 15 grams styrene and 85 grams of 1-decene, using 1 gram AlCl$_3$ as catalyst. Product properties are given in Table 4.

Example 10

Similar to Example 8 except the product was prepared from 30 grams styrene and 70 grams of 1-decene, using 1 gram AlCl$_3$ as catalyst. Product properties are given in Table 4.

TABLE 4

Product properties of styrene and 1-decene copolymers

|  | Example 8 | Example 9 | Example 10 | Example 11 | Example 12 |
|---|---|---|---|---|---|
| Olefins (O) | 1-C10 | 1-C10 | 1-C10 | 1-C12 | 1-C14 |
| Aromatics (A) | styrene | styrene | styrene | styrene | AMS |
| Wt % aromatics | 12.5 | 15 | 30 | 30 | 30 |
| End cap aromatics | toluene | toluene | toluene | toluene | toluene |
| Reaction temperature ° C. | 40 | 5–30 | 5–30 | 5–30 | 5–30 |
| Lube properties |  |  |  |  |  |
| V 100° C., cS | 34.05 | 44.51 | 58.17 | 67.94 | 35.47 |
| V 40° C., cS | 395.8 | 586.4 | 1119 | 1292 | 446.7 |
| V | 125 | 125 | 103 | 111 | 119 |
| Pour point, ° C. | −35 | −31 | −20 | −20 | −15 |
| Bromine no. | 1 | 2.3 | 2.0 | 2.4 | 3.1 |

TABLE 4-continued

Product properties of styrene and 1-decene copolymers

|  | Example 8 | Example 9 | Example 10 | Example 11 | Example 12 |
|---|---|---|---|---|---|
| Aniline point, ° C. | 132.9 | 133.9 | 107 | 114.7 | 129.9 |

Examples 8 to 10 demonstrate that copolymer of alpha-olefins and styrene produce lube products with lower aniline point than comparative examples, indicating a significantly improved base stock solvency and dispersancy.

Example 11

Preparation of Styrene and 1-dodecene Copolymer

Similar as Example 1, except that the mixture was prepared from 30 grams styrene, 70 grams 1-dodecene and 1 gram $AlCl_3$ as catalyst were used in the reaction. The product properties are summarized in Table 4. This example shows that other alpha-olefin copolymer with vinyl aromatics yields fluids with improved aniline point.

Example 12

Preparation of AMS and 1-tetradecene Copolymer

This product was prepared in similar procedure as Example 1, except that the mixture was prepared form 30 grams AMS, 70 grams 1-tetradecene and 4 grams $AlCl_3$ promoted with 120 microliters water was used as catalyst. The product properties are summarized in Table 4. These data show that 1-tetradecene can be used as starting alpha-olefins to copolymerize with vinyl aromatics.

Example 13

Preparation of AMS and 1-dodecene Without Toluene End Capping

A solution was prepared by mixing 2240 gms of dodecene (80 wt %) and 560 gms (20 wt %) of alpha-methyl styrene. This mixture was fed into a reactor over 6 hours. 3.85 gms of $AlCl_3$ was fed into the same reactor at 20 minute intervals over the 6 hour additional period. 0.2339 gms of water was also added to the reactor every 20 minutes over the 6 hour add period. The reaction mixture was maintained at 20° C. through external cooling of the reactor. After all the mixture was added the reaction mixture was left in the reactor for an additional 30 minutes.

The reaction mixture was quenched with 5% aqueous sodium hydroxide solution. The organic layer was washed with water separated and distilled at 280° C./<1 Torr, to remove unreacted alpha-methyl styrene, dodecene and dimers of dodecene. The product properties are summarized in the Table 5.

Example 14

Same as example-13, except the mixture was prepared by mixing 1960 gms of dodecene (70%) and 840 gms of AMS (30 wt %). The product properties are summarized in Table 5.

Example 15

Same as Example 13, except the mixture was prepared by mixing 1680 gms of dodecene (60 wt %) and 1120 gms of alpha-methylstyrene (40 wt %). The product properties are summarized in Table 5. The data in Table 5 demonstrate that high quality synthetic base stocks with high VI and low pour points were prepared.

TABLE 5

Copolymer lube properties made from AMS and 1-dodecene

|  | Example Number | | |
|---|---|---|---|
|  | 13 | 14 | 15 |
| Viscosity @ 100° C., cS | 37.8 | 36.37 | 37.27 |
| Viscosity @ 40° C., cS | 461.2 | 534.4 | 705.2 |
| VI | 125 | 105 | 87 |
| Pour point, ° C. | −33 | −27 | −24 |
| Bromine number | 4.3 | 3.5 | 2.8 |

What is claimed is:

1. A lubricant base stock comprising:
co-oligomers of an alpha olefin or mixture of alpha olefins and a olefinic substituted aromatic compound, the co-oligomers formed by co-oligomerizing in the presence of a Friedel-Crafts catalyst from about 1 to about 80 wt % of an olefinic substituted aromatic compound having the formula

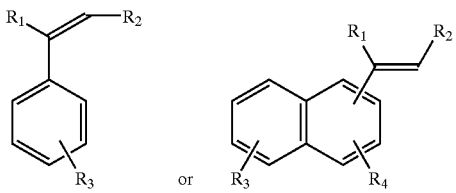

where $R_1$, $R_2$, $R_3$ and $R_4$ are independently H or a $C_1$ to $C_4$ alkyl group, and from 99 to about 20 wt % of an alpha olefin of from 6 to about 12 carbon atoms or a mixture of alpha olefin of from 6 to about 20 carbon atoms with at least 50% having less than 12 carbon atoms, the co-oligomerization being conducted at a temperature and under conditions selected from the group consisting of:

(a) continuously feeding the reactants into a reaction zone under steady state conditions with average residence time of olefin or mixture of olefin, olefinic substituted aromatic compound and catalyst in the range of from about 0.1 to about 10 hours; and (b) by introducing the olefin or mixture of olefins, olefinic substituted aromatic compound and catalyst substantially simultaneously into a reaction zone over an extended time period whereby substantially random co-oligomers are found.

2. The lubricant base stock of claim 1 wherein the co-oligomerization is conducted by introducing the olefin or mixture of olefins, olefinic substituted aromatic compound and catalyst substantially simultaneously into a reaction zone at feed rates of 50 to 2000 parts per hour for the olefin or mixture of olefins, 1 to 500 parts per hour for the olefinic aromatic compound and at 1 part per hour for the catalyst.

3. The lubricant base stock of claim 1 including continuously removing the co-oligomers from the reaction zone.

4. The lubricant base stock of claim 1, 2 or 3 wherein the co-oligomers are subsequently treated with an aromatic compound at a temperature and for a time sufficient to end-cap at least some of the oligomers with the aromatic compound.

5. The lubricant base stock of claim 1, 2 or 3 wherein the co-oligomers contain olefinic double bonds at least some of which are subsequently hydrogenated to give a fluid with a bromine number less than 2.

6. The lubricant base stock of claim 1 or 3 having a kinematic viscosity at 100° C. of form 3 to 300 cS and a viscosity index greater than 70.

7. The basestock of claim 6 wherein the mixture contains less than about 3 % of block oligomers.

8. The base stock of claim 7 wherein at least some of the oligomers are end-capped with an aromatic compound.

9. The base stock of claim 7 or 8 having a bromine number less than 2.

10. A process for preparing a lubricant base stock comprising: substantially simultaneously introducing, over an extended time period, an olefinic substituted aromatic compound, an alpha-olefin or mixture of alpha-olefins and a Friedl-Crafts catalyst into a reaction zone maintained at a temperature sufficient for co-oligomerization of the olefin or whereby a mixture of co-oligomers is formed, the alpha-olefin having from 6 to about 12 carbon atoms and the mixture of alpha-olefins having from 6 about 20 carbon atoms with at least 50% thereof having less than 12 carbon atoms and the olefinic substituted aromatic compound having the formula

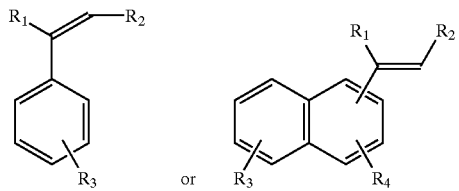

where $R_1$, $R_2$, $R_3$ and $R_4$ are independently H or a $C_1$ to $C_4$ alkyl group.

11. The process of claim 10 wherein the temperature is in the range of about -10 ° C. to about 150 ° C.

12. The process of claim 11 wherein said introducing is continuous and at a rate sufficient to provide an average residence time of olefinic substituted aromatic compound, olefin or mixture of olefins and catalyst of form about 0.1 to about 10 hours.

13. The process of claim 12 including continuously removing co-oligomers from the reaction zone.

14. The process of claim 13 including contacting the co-oligomers removed from the reaction zone with an aromatic compound or alkyl aromatic compound at a temperature in the range of about 0° C. to about 100° C. for a time sufficient to end-cap at least some of the co-oligomers with the aromatic or alkyl aromatic compound.

15. A lubricant composition comprising:

a major amount of co-oligomers of an alpha-olefin of 6 to 12 carbon atoms or mixture of alpha-olefin of having 6 to 20 carbon atoms with more than 50%thereof having less than 12 carbon atoms with an olefinic substituted aromatic compound having the formula

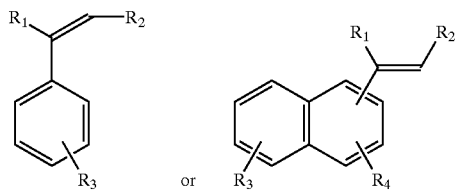

where $R_1$, $R_2$, $R_3$ and $R_4$ are independently H or a $C_1$ to $C_4$ alkyl group, the co-oligmers having a kinematic viscosity at 100° C. of from cS to 300 cS, wherein the co-oligmers contain less than about 3%of block oligomers, wherein the co-oligomers are prepared by co-oligomerizing the olefin or mixture of olefins and the olefinic aromatic compound at a temperature and under conditions selected from the group consisting of (a) continuously feeding the reactants into and removing the co-oligomers from a reaction zone under steady state conditions with average residence time of olefin or mixture of olefin, olefinic substituted aromatic compound and catalyst in the range of from about 0.1 to about 10 hours and (b) by introducing the olefin or mixture of olefins, olefinic substituted aromatic compound and catalyst substantially simultaneously into a reaction zone over an extended time period, whereby substantially random co-oligomers are formed; and an effective amount of one or more additives selected from the group consisting of antioxidants, viscosity index, improvers, antiwear additives, rust inhibitors, extreme pressure agents, antifoamants and dispersants.

16. The composition of claim 15 wherein at least some of the oligomers are end-capped with an aromatic or alkyl aromatic compound.

17. The lubricant composition of claim 15 or 16 wherein the co-oligomers have a bromine number less than 2.

18. In a grease composition including a lubricating base stock, a thickener and grease additives, the improvement wherein the base stock comprises co-oligomers of an alpha-olefin of 6 to 12 carbons or a mixture of alpha-olefins of 6 to about 20 carbon atoms in which at least 50% thereof have less than 12 carbons atoms, with an olefinic substituted aromatic compound having the formula

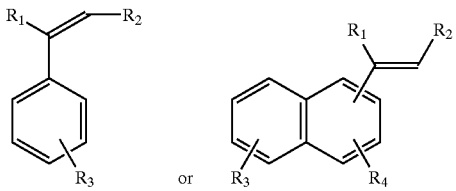

where $R_1$, $R_2$, $R_3$ and $R_4$ are independently H or $C_1$ to $C_4$ alkyl group, wherein the co-oligomers have a kinematic viscosity at 100° C. of from 5 cS to 300 cS and wherein the co-oligomers contain less than about 3% of block oligomers.

19. The improvement of claim 18 wherein at least some of the co-oligomers are end-capped with an aromatic or alkyl aromatic compound.

20. The improvement of claim 18 or 19 wherein the co-oligomers have a bromine number less than 2.

* * * * *